United States Patent [19]

Tsubota

[11] Patent Number: 5,795,912

[45] Date of Patent: Aug. 18, 1998

[54] THERAPEUTIC COMPOSITION FOR CORNEAL IMPAIRMENT

[75] Inventor: Kazuo Tsubota, Funabashi, Japan

[73] Assignee: Senju Pharmaceutical, Co., Ltd., Osaka, Japan

[21] Appl. No.: 815,511

[22] Filed: Mar. 12, 1997

Related U.S. Application Data

[63] Continuation of Ser. No. 670,236, Jun. 17, 1996, abandoned, which is a continuation of Ser. No. 427,902, Apr. 26, 1995, abandoned.

[51] Int. Cl.$^6$ .............................................. A61K 31/355
[52] U.S. Cl. .............................................. 514/458; 514/912
[58] Field of Search ............................ 514/458, 912

[56] References Cited

FOREIGN PATENT DOCUMENTS

| 0 127 471 | 12/1984 | European Pat. Off. . |
| 0 430 045 | 6/1991 | European Pat. Off. . |
| 0 616 809 | 9/1994 | European Pat. Off. . |
| 0 236 120 | 9/1997 | European Pat. Off. . |

OTHER PUBLICATIONS

Shimoyama et al., Investigative Ophthalmology & Visual Science, vol. 36, No. 4 15 Mar. 1995 p. 5696.

Senju Pharmaceutical, Database WPI Week 9201, Derwent Publications, Ltd., London GB AN 92–002618 JP–A–03 255 026 13 Nov. 1991.

Lazarenko et al., STN File Supplied: Chemical Abstracts AN = 85:91566.

Neuwirth–Lux et al., Australian and New Zealand Journal of Ophthalmology, vol. 15, pp. 309–314.

Saika et al., Graefe's Archive for Clinical and Experimental ophthalmology, vol. 231 (1993) pp. 221–227.

*Primary Examiner*—Zohreh Fay
*Attorney, Agent, or Firm*—Wenderoth, Lind & Ponack, L.L.P.

[57] ABSTRACT

This invention provides a therapeutic composition for corneal impairment which comprises a phosphoric acid diester compound of the following formula or a pharmacologically acceptable salt thereof,

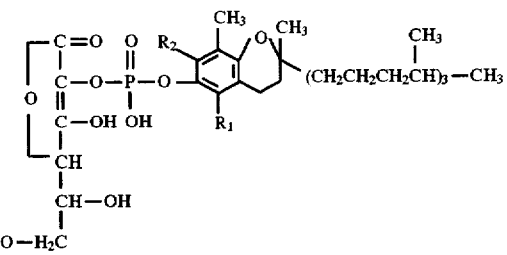

wherein $R_1$ and $R_2$ are the same or different and each represents a hydrogen atom or a methyl group.

The therapeutic composition of this invention is useful for the treatment of electricity-related ophthalmia, snow-related ophthalmia, corneal lesions caused by contact lens wearing, and corneal impairment associated with hypolacrimia.

1 Claim, 1 Drawing Sheet

THERAPEUTIC COMPOSITION FOR CORNEAL IMPAIRMENT

This application is a continuation application of application Ser. No. 08/670,236, filed Jun. 17, 1996, now abandoned which is a continuation application of application Ser. No. 08/427,902, filed Apr. 26, 1995, now abandoned.

BACKGROUND OF THE INVENTION

1. Field of the Invention

This invention relates to a useful therapeutic composition for corneal impairment. More particularly, this invention relates to a pharmaceutical composition useful for the therapy of corneal impairment which comprises an ascorbyl tocopheryl phosphate compound or a pharmacologically acceptable salt thereof.

2. Description of the Prior Art

The cornea consists of the ectoblastic epithelium, mesoblastic outer boundary layer (Bowman's membrane), substantia propria, inner boundary layer (Descemet's membrane), and endothelium. Being situated in the outermost part of the eyeball, the cornea is susceptible to various influences of the external environment so that it may sustain various injuries. As typical lesions of the cornea, ultraviolet light-induced keratitis (i.e. electricity-related ophthalmia and snow-related ophthalmia etc.) may be mentioned. Another corneal disease is dry eye (hypolacrimia, xerophthalmia, keratoconjunctivitis sicca) which develop as the corneal and conjunctival epithelia are injured in a deficiency of lacrimal secretion due to various causes such as many hours of eye-straining work, a dry environment, or oxidative substances (oxidants) in the atmosphere. The lacrimal secretions contain free-radical scavengers such as SOD (superoxide dismutase) in high concentrations and the injurious effect of these scavengers is thought to be amplified in dry eye because of the paucity of lacrimal secretion. Another type of corneal impairment is one caused by a sudden change in oxygen partial pressure due to contact lens wearing. It is suspected that in all of these types of corneal injuries, the free radicals generated by various causes exemplified above are a major contributory factor.

As therapeutic drugs for snow ophthalmia and other corneal diseases caused by ultraviolet radiation, among the above-mentioned diseases, either steroidal or non-steroidal antiinflammatory drugs have heretofore been indicated and used. Among them, steroidal antiinflammatory drugs are relatively more potent in antiinflammatory action but are disadvantageous in that their usage may entail serious adverse reactions. Therefore, these drugs must be administered only cautiously under close observation of the clinical course. On the other hand, non-steroidal antiinflammatory drugs have the disadvantage of being less potent than said steroidal drugs. Meanwhile, artificial tears are generally indicated in the treatment of hypolacrimia but this therapy does nothing but making up for a decrease in lacrimal secretion only for a brief time and cannot inhibit the above-mentioned free radicals, with the result that its therapeutic efficacy can hardly be considered to be sufficient.

The state of the art is that, for the above-mentioned diseases of the cornea, there is available no satisfactory drugs in terms of efficacy and side effect. Therefore, a need has been felt for a drug which would be more effective and useful for the treatment of these corneal diseases.

Under the circumstances summarized above, the inventor of this invention explored into the pharmacological actions of ascorbyl tocopheryl phosphate compounds and found that these compounds effectively inhibit the corneal impairment due to free radicals generated due to ultraviolet radiation or contact lens wearing and are useful for the treatment of electricity-related ophthalmia, snow-related ophthalmia, corneal lesions caused by contact lens wearing, and corneal impairment associated with hypolacrimia. This invention has been developed on the basis of the above finding.

SUMMARY OF THE INVENTION

This invention, therefore, is concerned with:

(1) A therapeutic composition for corneal impairment which comprises a phosphoric diester compound of the following formula or a pharmacologically acceptable salt thereof,

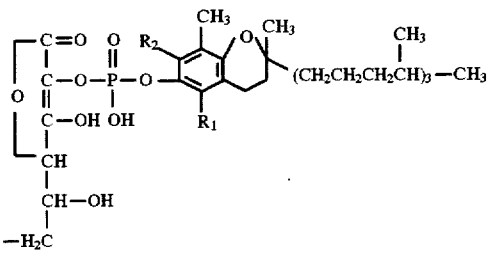

wherein $R_1$ and $R_2$ are the same or different and each represents a hydrogen atom or a methyl group;

(2) the therapeutic composition for corneal impairment as defined under (1) wherein the corneal impairment is a lesion associated with ultraviolet radiation;

(3) the therapeutic composition for corneal impairment as defined under (1) or (2) wherein the corneal impairment is electricity-related ophthalmia or snow-related ophthalmia;

(4) the therapeutic composition for corneal impairment as defined under (1) wherein the corneal impairment is a lesion associated with hypoladrimia; and (5) the therapeutic composition for corneal impairment as defined under (1) wherein the corneal impairment is a lesion associated with contact lens wearing.

Figure 1:
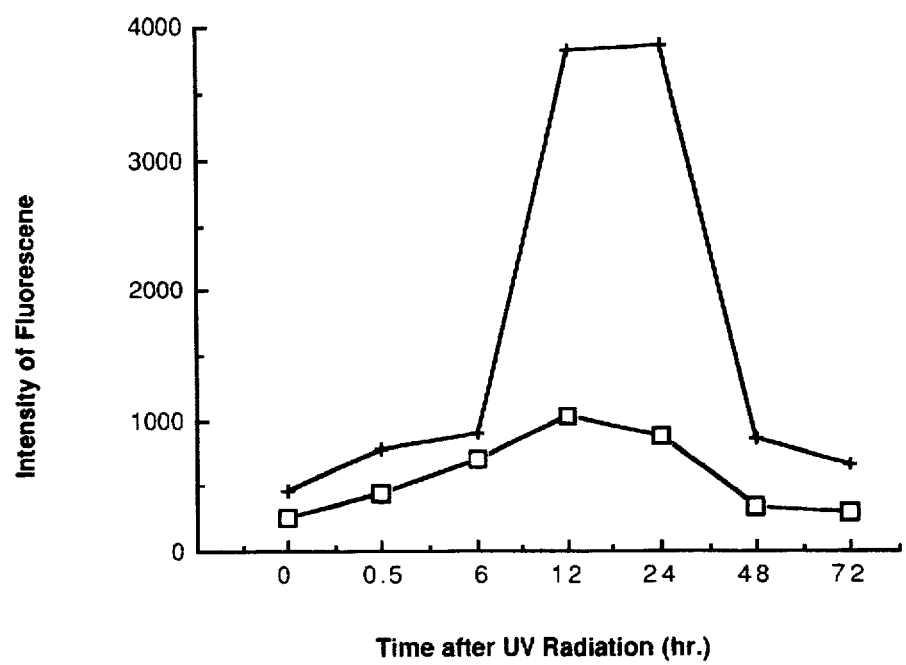
FIG. 1 is a graph showing the degrees of UV-induced corneal lesion in the control group and the present compound treatment group. The abscissa represents time and the ordinate represents the fluorescence intensity of fluorescein sodium penetrating into the rabbit cornea.

The symbols used in FIG. 1 represent:

□: the present compound treatment group

+: the control group

DETAILED DESCRIPTION OF THE INVENTION

The present compound for use in the therapeutic composition for corneal impairment according to this invention can be synthesized by inter alia the processes in Japanese Patent Publication H-2-44478 and Japanese Patent Application Kokai S-62-205091, or any process analogous therewith.

For the present compound as an active ingredient of the therapeutic composition for corneal impairment, a variety of uses such as an anticataract agent, a prophylactic and therapeutic agent for climacteric disturbance, a skin care cosmetic ingredient (Japanese Patent Publication H-2-44478), an antiinflammatory agent (Japanese Patent Publication H-1-27044), an antiulcer agent (Japanese Patent Application Kokai S-63-270626), a prophylactic and therapeutic agent for ischemic organic impairment (Japanese Patent Application Kokai H-2-111722) and a Maillard reaction inhibitor (Japanese Patent Application Kokai H-3-161444) are already known.

The present compound for use in the therapeutic composition for corneal impairment according to this invention may be a free compound or a pharmacologically acceptable salt. The pharmacologically acceptable salt typically includes salts with alkali metals such as sodium, potassium, etc. and salts with alkaline earth metals such as calcium, magnesium, and so on. However, any other salt can be likewise be employed only if it is pharmacologically acceptable.

The therapeutic composition for corneal impairment according to this invention may contain one or more species of the present compound according to the intended use and need.

The compound for use as an active ingredient in the therapeutic composition for corneal impairment according to this invention is a very safe substance with an extremely low toxic potential and, as such, can be used with advantage for the purposes of this invention. [e.g. the $LD_{50}$ values of L-ascorbyl DL-α-tocopheryl phosphate potassium (hereinafter referred to briefly as EPC-K) $\geq$ 5 g/kg p.o. (rats) and $\geq$ 100 mg/kg i.v. (rats)].

The corneal lesion that can be treated with the therapeutic composition for corneal impairment according to this invention includes electricity-related ophthalmia, snow-related ophthalmia, corneal lesions caused by contact lens wearing, and corneal impairment associated with hypolacrimia.

The therapeutic composition for corneal impairment of this invention can be administered either orally (e.g. tablets etc.) or otherwise (e.g. ophthalmic solutions, ophthalmic ointments, injections, etc.) for the treatment of the above-mentioned corneal impairment. The dosage form in which the therapeutic composition of this invention can be provided includes ophthalmic solutions, ophthalmic ointments, tablets, granules, powders, capsules, injections and so on. These dosage forms can be manufactured by the established pharmaceutical procedures. In such dosage forms, a variety of additives such as excipients, binders, disintegrators, dispersants, reabsorption promoters, buffers, surfactants, solubilizers, preservatives, emulsifiers, isotonizing agents, stabilizers and pH control agents can be incorporated in appropriate amounts.

In application of the present compound as a therapeutic drug for corneal impairment, its dosage depends on the species of compound, the type of disease to be treated, the patient's age and body weight, clinical manifestations that must be controlled, and the dosage form but recommended daily injection dose for an adult patient is about 1 mg–100 mg. In the case of an oral preparation, about 10 mg–1000 mg per dose can be administered a few times a day to the average adult. In the case of an ophthalmic solution, a few drops of a solution containing about 0.01–5% (w/v), preferably about 0.05–2% (w/v), of the present compound can be instilled into the eye several times daily for the average adult. In the case of an ophthalmic ointment, a formulation containing about 0.01–5% (w/w), preferably about 0.05–2% (w/w), of the present compound can be applied several times daily for the average adult.

Unless contrary to the spirit and object of this invention, the pharmaceutical composition of this invention may further contain other therapeutic drugs for corneal impairment and/or other kinds of medicinal substances.

EXAMPLES

The following examples and formulation examples are intended to describe this invention in further detail.

Example 1

Inhibitory effect of the present compound on UV-induced corneal lesions in rabbits The inhibitory effect of the present compound on UV-induced corneal lesions in rabbits was evaluated. Test substance: L-Ascorbyl DL-α-tocopheryl phosphate potassium (abbreviation: EPC-K). Method: White rabbits were used; 4 animals assigned to the present compound treatment group and 3 assigned to a control group (the nictitating membrane was excised beforehand).

For UV irradiation, Hoya-Schott's HLS200U (dominant wavelength 365 nm) equipped with a 200 W mercury-xenon lamp as the light source was used. Ushio Electric's Unimeter UIT-101 was used for the determination of luminous energy.

One eye of each rabbit was kept open with an eye speculum and set at a distance of 43 cm from the light source so that the irradiation energy would be 0.024 $J/cm^2$. The eye was irradiated with ultraviolet light under the conditions of 0.2 $mW/cm^2$ and 2 minutes. The fellow eye was protected with an eye patch.

After UV irradiation, the vehicle (2.6% concentrated glycerin solution) was instilled in the eyes of rabbits in the control group 3 times daily and 0.1% EPC-K (dissolved in 2.6% concentrated glycerin solution) was instilled as often into the eyes of rabbits in the present compound treatment group.

The degree of rabbit corneal lesion was evaluated by the following method[1]. Using fluorescein as a tracer, the fluorescence intensity of the tracer dye penetrating into the cornea within a predetermined region was measured for a quantitative assessment of the barrier function of the corneal epithelium (The corneal epithelium has a barrier function[2] to restrict penetration of any substance into the deep layer of the cornea and when an erosion or other injury occurs in the corneal epithelium, this barrier function is compromised so that the penetration of the substance into the depth of the cornea is increased). Thus, at 0, 0.5, 6, 12, 24, 48 and 72 hours after UV irradiation, fluorescein sodium was instilled into the eye and the fluorescence intensity of the fluorescein sodium that had penetrated into the cornea was measured with a Kowa anterior fluorophotometer.

1) Norihiko Yokoi et al.: Quantitative evaluation of corneal epithelial barrier function with a new fluorophotometer, Journal of the Eye, 10(8); 1357–1363, 1993

2) Klyce SD and Crosson CE: Transport processes across the rabbit corneal epithelium, a review. Curr Eye Res 4 4;427–432, 1985.

Results: The results are shown in Table 1.

TABLE 1

Inhibitory effect of the present compound on UV-induced corneal lesion

| group | Time after irradiation (in hours) | | | | | | |
|---|---|---|---|---|---|---|---|
| | 0 | 0.5 | 6 | 12 | 24 | 48 | 72 |
| Control group | 457 | 791 | 899 | 3813 | 3860 | 870 | 655 |
| Present compound treatment group | 259 | 447 | 695 | 1038 | 875 | 343 | 311 |

Each figure in the table denotes the intensity of fluorescence.

FIG. 1 is a diagrammatic version of Table 1. It will be apparent from Table 1 and FIG. 1 that the drug of this invention effectively inhibits UV-induced corneal lesion.

Formulation Example 1 Tablets for oral administration

| | |
|---|---|
| EPC-K | 100 mg |
| Lactose | 75 mg |
| Starch | 20 mg |
| Polyethylene glycol 6000 | 5 mg |

The above components per tablet are mixed in the routine manner to provide tablets. Where necessary, the tablets may be sugar-coated.

Formulation Example 2 Injection

| | |
|---|---|
| EPC-K | 200 mg |
| Mannitol | 5.0 g |
| 1N-Sodium hydroxide | q.s. |
| Distilled water | to make 100 ml |
| | pH 6.5 |

The above components are mixed and filtered through a membrane filter in the routine manner. The filtrate is aseptically filled in glass vials, 5 ml per vial, followed by sealing by fusion to provide an injectable preparation.

Formulation Example 3 Ophthalmic solution

| | |
|---|---|
| EPC-K | 0.5 g |
| Boric acid | 1.8 g |
| Benzalkonium chloride | 0.005 g |
| 1N-Sodium hydroxide | q.s. |
| Sterilized pure water | to make 100 ml |
| | pH 7.3 |

The above components are mixed in the routine manner to provide an ophthalmic solution.

The pharmaceutical composition of this invention is of use as a therapeutic drug for corneal impairment such as electricity-related ophthalmia, snow-related ophthalmia, corneal lesions due to contact lens wearing and corneal impairment associated with hypolacrimia.

What is claimed is:

1. A method of treating corneal impairment selected from electricity-related ophthalmia and snow-related ophthalmia, which comprises administering to a human in need thereof an effective amount of a compound of the formula

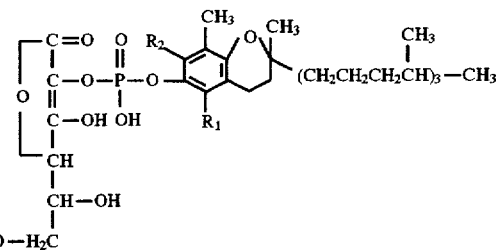

wherein $R_1$ and $R_2$ are the same or different and each represents a hydrogen atom or a methyl group; or a pharmacologically acceptable salt thereof.

* * * * *